United States Patent [19]
Le Ribault

[11] Patent Number: 5,391,546
[45] Date of Patent: Feb. 21, 1995

[54] COMPOSITION COMPRISING ORGANO-SILICON COMPOUNDS FOR THERAPEUTIC USE

[75] Inventor: Loic Le Ribault, La Teste De Buch, France

[73] Assignees: Michel B. Lamothe; Rene Nardou, France; a part interest

[21] Appl. No.: 46,466

[22] Filed: Apr. 12, 1993

Related U.S. Application Data

[63] Continuation of Ser. No. 708,841, May 30, 1991, abandoned, which is a continuation of Ser. No. 283,026, Dec. 9, 1988, abandoned, which is a continuation of Ser. No. 944,506, Dec. 22, 1986, abandoned.

[30] Foreign Application Priority Data

Dec. 23, 1985 [FR] France ................ 85 19204

[51] Int. Cl.⁶ .................. A61K 31/695; A61K 33/04
[52] U.S. Cl. ...................................... 514/63; 424/711
[58] Field of Search ................ 514/63; 424/711

[56] References Cited

U.S. PATENT DOCUMENTS 3,764,673 10/1973 Andersen et al. ............... 514/63
4,148,885 4/1979 Renoux et al. ................ 424/162

FOREIGN PATENT DOCUMENTS 2158068 2/1975 France .
2160293 2/1975 France .
2230376 8/1976 France .
1388330 3/1975 United Kingdom ...... A61K 31/695

OTHER PUBLICATIONS

Unlisted Drugs, vol. 31, No. 4, Apr. 1979, p. 55.
Rakel, Conn's Current Therapy, 1986, pp. 651–654.

Primary Examiner—Raymond J. Henley, III
Assistant Examiner—William R. A. Jarvis
Attorney, Agent, or Firm—Robert J. Koch; Peter J. Davis

[57] ABSTRACT

This invention discloses a pharmaceutical composition comprising organo-silicon compounds and sodium or magnesium hyposulfite. The composition is effective at treating asthma and manifestations of allergy in general, sinusitis, herpes, viral hepatitis, and viral diseases in general.

8 Claims, No Drawings

COMPOSITION COMPRISING ORGANO-SILICON COMPOUNDS FOR THERAPEUTIC USE

This is a continuation application of application Ser. No. 07/708,841, filed May 30, 1991, abandoned, which is a continuation application of application Ser. No. 07/283,026, filed Dec. 9, 1988, abandoned, which is a continuation of application Ser. No. 06/944,506, filed Dec. 22, 1986, abandoned.

This invention relates to new compositions for therapeutic use, particularly useful for the treatment of asthma and manifestations of allergy in general, as well as sinusitis, herpes and viral hepatitis, Herpes Zoster and viral diseases in general in man.

Organo-silicon compounds have already been used in human therapy for numerous years.

These water-soluble, atoxic compounds easily pass through the epidermis and dermis by local application (GUEYNE, DUFFAUT and QUILICHINI, Thérapie, 1962, 17, 417).

Numerous therapeutic properties of organo-silicon compounds used alone have been described in several patents (in particular French patents published under No. 2,158,068, 2,160,293 and 2,230,376, which are incorporated herein by reference).

French patent No. 2,230,376 describes organo-silicon compounds according to the formula:

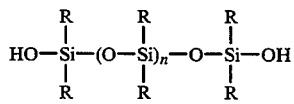

wherein R is an aliphatic, aromatic, cyclic or heterocyclic group; and n is a whole number between 0 and 20. French patent No. 2,158,068 describes organo-silicon compounds according to the formula:

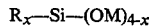

wherein

R is alkyl, acyl or aryl;

x is a whole number between 0 and 3; and

M is a hydrogen atom or an alkali metal.

These organo-silicon compounds are administered, according to the above patents, by the intramuscular or intravenous route, or else by electrophoresis, the active principle then being in solution in water (isotonic solution), possibly with addition of an alcohol or a polyalcohol, such as glycerol, and/or a sodium salt of a pharmaceutically acceptable organic acid.

It has already been demonstrated in particular in the above patents that certain substances of various natures potentialise and broaden the action spectrum of organo-silicon compounds.

It has now been unexpectedly found that a new composition for therapeutic use can be made by combining in the appropriate proportions one or several organo-silicon compounds with sodium or magnesium hyposulfite (or thiosulfate).

It has also been found that compositions of this type are quite particularly useful against asthma and manifestations of allergy in general, sinusitis, herpes and viral hepatitis, Herpes Zoster and viral diseases in general, against which they have a specific action, and that the compositions thus made can be administered simply by the transcuataneous route in man and animals.

The first object of the invention is a composition for therapeutic use particularly useful for the treatment of asthma, sinusitis, herpes and viral hepatitis among others, wherein it includes in aqueous solution:

(1) at least one organo-silicon compound represented by either of the two formulas:

(A)

or

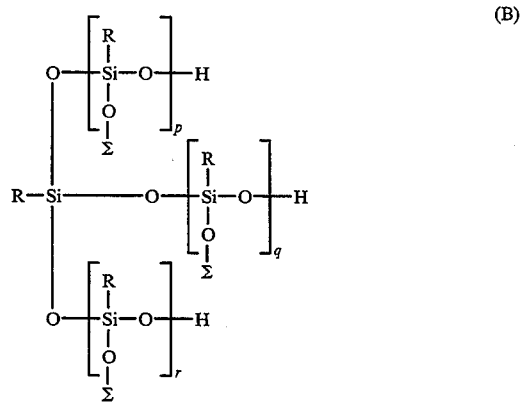

(B)

where:

n is a whole number between 1 and 1000 and, preferably, between 1 and 50;

p, q, r are whole numbers between 0 and 1000 and, preferably, between 0 and 60;

R and R' representing, independently of one another, a saturated or unsaturated linear, branched or cyclic group and possibly including heteroatoms, or an aromatic, hetereroaromatic, arylaliphatic, or heteroarylaliphatic group, possibly substituted by functional groups, it being possible also for R to be OH, OR or OSiR$_3$.

Σ being R or H or SiR$_3$;

Σ' being chosen from R and more particularly CH$_3$ or OR, or OH or OSIR$_3$, (where R is such as is described above), or alkali metal or addition salts with a pharmaceutically acceptable acid, of said compound, the organo-silicon compound(s) being used at a concentration varying between $10^{-5}$ and $10^{-1}$ atom-gram of silicon per liter and more particularly between $10^{-4}$ and $10^{-2}$ atom-gram/liter of water, and (2) sodium hyposulfite (Na$_2$S$_2$O$_3$, 5 H$_2$O) or magnesium hyposulfite, the ratio of (1) to (2) being 5 to 50 g of hyposulfite per liter of organo-silicon solution, preferably about 20 g/liter of organo-silicon solution.

It is noted that the compounds disclosed in French patent Nos. 2,230,376 and 2,158,068 fall within the scope of the above-described formulae for the organo-silicon compound.

As a variant, the composition according to the invention can also include in an appropriate proportion to neutralize or possibly stabilize these compounds one or several organic acids (or their salts, in particular their alkali salts), such as for example salicylic acid, citric acid, propionic acid, aspartic acid, glutaric acid and/or glutamic acid. However, it should be noted that salicylic acid must not be used for the treatment of patients allergic to phenols and salicylic acid in particular and that, in such an eventuality, this acid may quite well be replaced by citric acid or its salts, as is shown later in the examples.

An organic acid or its salt is used in concentrations varying between $10^{-5}$ and $10^{-1}$ molecule-gram or more per liter, particularly between $10^{-2}$ and $10^{-4}$ molecule-gram per liter.

In all cases, it has found to be preferable for the pH of the solution to be between 3 and 7, or, better, between 3 and 5.

The organo-silicon compounds represented by the above formula are products known in themselves.

To make compositions according to the invention use can be made either of those available in commerce, or their known precursors, which yield them by hydrolysis, such as for example silazanes or corresponding alkoxysilanes (see in particular document FR-A-2,230,376 on this subject).

Sodium or magnesium hyposulfite may be combined with organo-silicon compounds by addition to a suitably proportioned solution of these, either in its solid state or in the form of a suitably proportioned aqueous solution, either originally or during application and in particular during the utilization of the compositions according to the invention for therapeutic purposes.

The composition according to the invention may therefore consist either of a unique product containing the organo-silicon compound and the hyposulfite, or a two-component product containing separately the organo-silicon compound and the hyposulfite, whose mixture can then be freshly prepared just before use.

The composition can be made available to users in bottles or ampoules which constitute unit doses containing a quantity of product dosed for each administration.

The unit doses of the complete composition recommended for each transcutaneous administration are advantageously 10 cm$^3$.

The compositions can be supplemented by neutralizing agents and/or preservatives compatible with the active principles, such as those indicated above, as well as by other constituents, such as dyes, perfumes or other excipients, which the man skilled in the art is able to chose and incorporate as needed according to his knowledge of the subject matter.

From trials carried out in man, it has been established that the application of organo-silicon compounds combined with sodium or magnesium hyposulfite to the skin, for example, by dabbing compositions according to the invention, has a transcutaneous action exerting a pharmacologically effective action against attacks of asthma and manifestations of allergy in general, sinusitis, herpes, viral hepatitis, Herpes Zoster and viral diseases in general.

Trial results have shown that compositions according to the invention are particularly indicated and exceptionally effective without having any appreciable toxicity (as will be shown later), for the treatment and/or the prevention of asthma, headaches and manifestations of allergy in general, sinusitis, herpes, viral hepatitis, Herpes Zoster and viral diseases in general.

As an indication, the utilisation modes that can be recommended are:

Application of a cotton compress (about 5 cm by 7 cm) soaked with the composition according to the invention to the painful or deficient area or any other part of the body. The compress is covered with a sheet of plastic material or any other material that can preserve the moisture by preventing evaporation. The compress is applied for a period of between 8 and 12 hours per day (or overnight, for example).

Massage with a composition according to the invention applied in the form of a cream according to a known technique.

Dabbing the cutaneous area with a pad soaked with the composition according to the invention.

This dabbing is carried out 2 to 4 times a day, for example, on the forearm, where the blood vessels are more apparent. For it has been demonstrated that the composition according to the invention easily passes through the epidermis.

The composition can also be applied simultaneously, locally or not, by ionokinesis, to the painful or deficient area.

The ionokinesis apparatus consists of a direct current generator (about 10–15 milliamperes), provided with a device for establishing or shutting off the current gradually and maintaining a constant amperage for the duration of a session.

The amperage is gradually brought to 10 mA and maintained for 20 minutes before being gradually lowered and then turned off.

In certain cases the amperage can be raised up to 25 mA, it then being possible for the duration of the session to be up to 30 minutes.

The generator is connected to two carbon electrodes or other commonly employed materials for electrodes used in ionokinesis treatments. Although the surface area of the electrode may be very variable, it is commonly of the order of 200 cm$^2$.

Each of the electrodes is surrounded by cotton-wool which is impregnated with the composition according to the invention.

The electrode connected to the negative pole of the generator is applied to any part of the body, but preferably to the deficient or painful area. It is maintained in contact with the bandage.

The other electrode, connected to the positive pole of the generator, can be applied to any place on the skin or simply held in the hand, the contact surface area being as large as possible. In certain particular cases, the polarity of the electrodes is reversed during a session.

It should be pointed out that a treatment requires 10 to 30 sessions at 24 to 72 hour intervals, the most common rate being 2 to 3 sessions per week.

The treatment is absolutely painless. However, some susceptible subjects experience a prickling sensation near the electrodes during sessions. No local or general reaction of the organism has been noted except slight erythema in the electrode application area.

However, when a subject is slightly allergic to phenolic derivatives, a solution not containing this type of derivative must be chosen.

Intramuscular injection may also be given.

To assess the acute toxicity of a potassium methylsiliconate+sodium hyposulfite composition, the following experimentation described hereinafter was carried out. The composition administered was in the form of 1.5% (weight/volume) aqueous solution. The experimentation consisted in determining the LD$_{50}$ for female mice by sub-cutaneous administration. It was conducted under the conditions described below:

I-Animals

150 Swiss race female mice of 30 g average weight were taken from a batch of animals that had been received fifteen days ago, and therefore well-accustomed to the animal house.

There were divided into 6 batches of 25 animals and numbered from 1 to 25 within each batch, the batches themselves being identified by the letters A to F.

The animal house conditions were as follows:
feed and beverage: ad libitum
type of feed: commercial complete feed (Extra Labo)
average temperature: 21° C.
relative humidity: 73%
experiment start time: 9 hours II-Doses administered It was established from a preliminary experiment performed on some 25 animals that doses of between 30 and 40 ml/kg showed a greater or lesser mortality resulting in the following doses being selected:

25 ml/kg, or 375 mg/kg of potassium methylsiliconate+sodium hyposulfite for Group A;

30 ml/kg, or 450 mg/kg of potassium methylsiliconate+sodium hyposulfite for Group B;

35 ml/kg, or 525 m/kg of potassium methylsiliconate+sodium hyposulfite for Group C.

40 ml/kg, or 600 mg/kg of potassium methylsiliconate+sodium hyposulfite for Group D;

45 ml/kg, or 675 mg/kg of potassium methylsiliconate+sodium hyposulfite for Group E;

50 ml/kg, or 750 mg/kg of potassium methylsiliconate+sodium hyposulfite for Group F.

Subcutaneous injection was chosen as the mode of administration.

III-Results

BATCH A: No mortality, nor any external sign of toxicity appeared, neither immediately after administration, nor subsequently, that is, during the fifteen days for which the animals were kept under surveillance. The behaviour and general condition of these were quite normal.

BATCH B: Just as for Batch A, no mortality, nor any behavioural trouble were observed. Their general condition was excellent during the period following administration of the potassium methylsiliconate+sodium hyposulfite composition.

BATCH C: 6 animals of this group had died under comparable circumstances and in times ranging from 45 minutes to 90 minutes after administration. The clinical ante-mortem signs were prostration, need for isolation, dulling of the fur and onsets of shivering (more or less violent, but without convulsions) starting 15 to 20 minutes before death, which was preceded by a few accentuated bounds.

Post-mortem examination showed that all the internal organs had a normal appearance: in particular, the liver, spleen, pancreas, kidneys and adrenal capsules did not reveal any visible anomalies. However, it was noted that the bladder was regularly empty and that the heart had stopped in the systole position. The lungs were slightly pinkish. There was no particular sign at the injection point.

The majority of the surviving animals did not appear to have been affected by the product. Three showed slight signs of discomfort, which soon died away. However, the fur of all the animals of this group was dull for 24 hours.

Thereafter, the behaviour and general conditions of the surviving animals reverted to normal for fifteen days after administration.

BATCH D: 11 animals of this group died under conditions and in times identical with those of Group C. The ante-mortem clinical signs and post-mortem anatomical examinations were quite comparable to these. Four animals showed transient signs of discomfort. The fur of all the surviving animals had a dull appearance for 24 hours; thereafter, their behaviour and general condition were completely normal during the observation period.

BATCH E: 14 animals of this group died under conditions and in times identical with those of the preceding groups, with quite comparable clinical and anatomical pictures.

Two animals showed momentary discomfort. All the survivors had a dull fur for 24 hours. Thereafter, as for the survivors of Batches C and D, complete normalization of behaviour and general conditions were noted throughout the observation period.

BATCH F: In this group 17 animals died under circumstances and in times comparable to those of Groups C, D and E.

The ante-mortem behaviour noted and the post-mortem examinations showed that the observations were an exact copy of those of the preceding groups. Four animals showed momentary discomfort.

All the survivors had a dull fur for 24 hours. They then reverted to completely normal behaviour and general condition during the observation period.

Following the observation period of fifteen days, all the animals surviving these trials were alive and in good health after a period of one month.

IV-Discussion and interpretation of results.

From this experimentation, it was possible to calculate the percentage mortality in accordance with the dose administered:

Batch A mortality: 0%
Batch B mortality: 0%
Batch C mortality: 24%
Batch D mortality: 42%
Batch E mortality: 56%
Batch F mortality: 67%

The subcutaneous $LD_{50}$ for the mouse was therefore well between two points below and two points above its value. The probit/log chart (percentage mortality against logarithm of dose in mg/kg) plotted from these results enabled the $LD_{50}$ to be established at 645 mg/kg for the composition of the invention tested.

In addition, it has been possible to determine a limit at which the first reversible signs of toxicity appear, such as somnolence and need for isolation. This limit was evaluated at 380 mg/kg.

V-Conclusion

The compositions according to the invention are seen to be little toxic, since the doses which are recommended to be used for therapeutic purposes are hundred times lower than the dose which causes the first signs of toxicicity to appear.

The invention is described and illustrated in detail in the examples hereinafter, which in no way limit it and which include all the information concerning the compositions and their preparation and the properties revealed by pharmacological trials relating to various diseases in man.

EXAMPLE 1

J. R., suffering from herpetic keratitis with ulceration of the cornea, intense lacrymation and major vasodilation of the conjuctiva, was treated with cortisone eye wash, without any result.

For three days, two daily eye baths were given with a solution according to the invention consisting of the following:

1 g of salicylic acid was introduced into a 1-liter beaker and 700 ml of distilled water added to it.

Onto this solution was poured slowly, while stirring vigorously, 1.2 ml of 45% dry extract solution of potassium methylsiliconate.

The solution was brought to a pH of 4.7 and made up to 1 liter with distilled water. 20 g of sodium sodium hyposulfite were then added.

Following the application of this treatment, with a solution made isotonic and buffered, the inflammation disappeared in 24 hours and cicatrization was found to be complete after 7 days.

Examined again after three months, the patient did not show any after-effects.

EXAMPLE 2

Mrs. L. Z. very frequently (about twice a month) suffered from a hepatic eruption on the upper lip.

A series of local applications were made with a cotton-wool pad soaked with the solution of the composition according to the invention, made as follows:

1 g of citric acid was introduced into a 1-liter beaker and 700 ml of distilled water added to it. Onto this solution was poured slowly, while stirring vigorously, 1.7 ml of a solution of 45% dry extract potassium siliconate. The solution was brought to a pH of 4.7 and made up to 1 liter with distilled water. 20 g of sodium hyposulfite were finally added to the whole.

At a rate of three applications of a cotton-wool pad soaked with the above composition, cicatrization was found to have taken place without any visible trace remaining after 7 days, and no recurrence was noted after a waiting time of three months.

EXAMPLE 3

Mr. M. L. had contracted recurrent genital herpes which affected the glans and prepuce.

A series of local applications to the lesion were made using a solution of the composition according to the invention, made as follows: 1 g of citric acid was introduced into a 1-liter beaker and 800 ml of distilled water added to it. Onto this solution were poured gradually, stirring vigorously, 2.5 ml 30% dry extract sodium methylsiliconate. The solution was brought to a pH of 4.7 and made up to 1 liter with distilled water and 20 g of sodium hyposulfite added.

Three local applications were made daily by dabbing with a cotton-wool pad soaked with the solution described above.

After a week of this treatment, it was found that the eruption had disappeared, without leaving any visible trace. After three months, there were no signs of recurrence.

EXAMPLE 4

Miss L. B., with recurrent herpes of the vulva suffered every month a painful eruption with major oedema affecting the labia minor and the labia major one week before menstruation.

A series of local applications to the lesion were made using the composition according to the invention, made as follows:

Into a 1-liter beaker containing 500 ml of water, previously cooled with crushed ice, were introduced slowly, while stirring vigorously, 0.65 g of dimethylchlorosilane and 0.85 g of sodium bicarbonate. A check was made that the pH was about 7. The solution thereby obtained was homo-geneous.

1.1 g of sodium salicylate was added slowly, while stirring vigorously. The solution was brought to a pH of 4.7 and made up to 1 liter with distilled water, and finally 20 g of sodium hyposulfite were added.

Two local applications were made daily during the eruptive phase by dabbing with a pad of cotton-wool soaked with the solution described above. The patient experienced very rapid relief, and the oedema disappeared in a few days.

In the following three months there was no irruption during the pre-menstrual period.

EXAMPLE 5

Mr. R. B. was suffering from a sudden onset of jaundice. Laboratory analyses confirmed the diagnosis of viral hepatitis. The transminases level was high: 1100.

A cotton-wool compress soaked with composition according to the invention, covered with a plastic sheet, described above in Example 3 was applied in the region of the liver. This compress was maintained in position for ten hours per day.

After six days, the jaundice had definitely regressed, and the transminases level dropped to 50.

After two months, the patient no longer showed any clinical or biological sign of hepatitis.

EXAMPLE 6

Mr. E. F. suffered from attacks of nocturnal dispnea with suffocation.

Seven applications were made by dabbing his forearm in the evening before he went to bed with a cotton-wool pad soaked with the composition according to the invention, described in Example 1. These applications were combined with nasal instillations with the same solution.

It was found that attacks decreased in intensity after 4 days and gradually ceased altogether.

A maintenance treatment of one application per week was continued for two months. In addition, the patient was advised during this period to resume dabbing (combined with nasal instillation) if there was the least breathing discomfort, as a preventive measure.

After three months, the patient no longer suffered from any attacks and the disease had not shown any signs of reccurrence for eight months.

EXAMPLE 7

Mrs. B. P. had undergone a series of examinations which had revealed viral hepatitis. Among these, chemical analyses of the blood in particular gave the following results:

Transminases:
S.G.O.T: 1290 IU/l
S.G.P.T.: 2170 IU/l

The patient then underwent treatment with the composition according to the invention such as is described above in Example 1, consisting of massage of the region of the liver, 4 times a day, with a cream made with this composition.

Five days later the results of the blood analyses were the following:

Transminases:

S.G.O.T.: 50 IU/l
S.G.P.T.: 210 IU/l

EXAMPLE 8

Mrs. Y. L. had suffered from sinusitis for several years. Although during this period she had had several operations (removal of tonsils, ablations of adenoids) and various treatments and examinations without any durable results.

After a further major attack against which conventional treatments had not given any appreciable result, the patient was given treatment by a first application of the composition according to the invention as described in Example 2 above, by rubbing the top of the nose with a cream made with this composition. This application was repeated 4 times a day. One hour after the first application nasal discharges obliged the patient to blow her nose continuously up to evening. As early as the following day the patient felt "freed" and breathed normally. No further attack of sinusitis has been recorded since then.

What is claimed is:

1. A composition comprising in aqueous solution:
   (1) at least one organo-silicon compound represented by either of the formulas:

$$R^1_x\text{—}Si\text{—}(OM)_{4-x} \quad (A)$$

or $$HO\text{—}\underset{R}{\overset{R}{Si}}\text{—}(O\text{—}\underset{R}{\overset{R}{Si}})_n\text{—}O\text{—}\underset{R}{\overset{R}{Si}}\text{—}OH \quad (B)$$

wherein
   R is aliphatic, aromatic, cyclic or heterocyclic;
   n is a whole number between 0 and 20;
   $R^1$ is alkyl, acyl or aryl;
   x is a whole number between 0 and 3;
   M is a hydrogen atom or an alkali metal;
   said organo-silicon compound being used at a concentration between $10^{-5}$ and $10^{-1}$ atom-gram of silicon per liter $H_2O$; and
   (2) sodium hyposulfite ($Na_2S_2O_3$—5 $H_2O$) or magnesium hyposulfite;
   the ratio of hyposulfite to organo-silicon solution being 5 to 50 grams of hyposulfite per liter of organo-silicon solution.

2. A composition according to claim 1 wherein the organo-silicon compound is potassium methylsiliconate.

3. A composition according to claim 1 wherein the organo-silicon compound is potassium siliconate.

4. A composition according to claim 1 wherein the organo-silicon compound is sodium methylsiliconate.

5. A method for the therapeutic treatment of a human suffering from asthma, sinusitis, herpes and/or viral hepatitis, comprising administering to said human a therapeutically effective amount of a composition comprised of:
   (1) at least one organo-silicon compound represented by either of the formulas:

$$R^1_x\text{—}Si\text{—}(OM)_{4-x} \quad (A)$$

or $$HO\text{—}\underset{R}{\overset{R}{Si}}\text{—}(O\text{—}\underset{R}{\overset{R}{Si}})_n\text{—}O\text{—}\underset{R}{\overset{R}{Si}}\text{—}OH \quad (B)$$

wherein
   R is aliphatic, aromatic, cyclic or heterocyclic;
   n is a whole number between 0 and 20;
   $R^1$ is alkyl, acyl or aryl;
   x is a whole number between 0 and 3;
   M is a hydrogen atom or an alkali metal;
   said organo-silicon compound being used at a concentration between $10^{-5}$ and $10^{-1}$ atom-gram of silicon per liter $H_2O$; and
   (2) sodium hyposulfite ($Na_2S_2O_3$—5 $H_2O$) or magnesium hyposulfite;
   the ratio of hyposulfite to organo-silicon solution being 5 to 50 grams of hyposulfite per liter of organo-silicon solution.

6. A method according to claim 5 wherein the organo-silicon compound is potassium methylsiliconate.

7. A method according to claim 5 wherein the organo-silicon compound is potassium siliconate.

8. A method according to claim 5 wherein the organo-silicon compound is sodium methylsiliconate.

* * * * *